United States Patent [19]

Hetzel

[11] 4,033,351
[45] July 5, 1977

[54] BIPOLAR CUTTING ELECTRODE FOR HIGH-FREQUENCY SURGERY

[75] Inventor: Gert Hetzel, Erlangen, Germany

[73] Assignee: Siemens Aktiengesellschaft, Berlin & Munich, Germany

[22] Filed: Sept. 14, 1976

[21] Appl. No.: 723,170

Related U.S. Application Data

[63] Continuation of Ser. No. 570,792, April 23, 1975, abandoned.

[30] Foreign Application Priority Data

June 14, 1974 Germany .......................... 2428886

[52] U.S. Cl. ...................... 128/303.14; 128/303.18
[51] Int. Cl.² ......................................... A61B 17/36
[58] Field of Search ................. 128/303.14, 303.17, 128/303.13, 303.18, 405

[56] References Cited

UNITED STATES PATENTS

| 1,814,791 | 7/1931 | Ende | 128/303.18 |
| 1,916,722 | 7/1933 | Ende | 128/303.18 |
| 2,275,167 | 3/1942 | Bierman | 128/303.17 |
| 2,611,365 | 9/1952 | Rubens | 128/303.13 |
| 3,460,539 | 8/1969 | Anhalt | 128/303.17 |
| 3,858,586 | 1/1975 | Lessen | 128/303.17 |

FOREIGN PATENTS OR APPLICATIONS 243,478  7/1946  Switzerland ................... 128/303.18

Primary Examiner—Robert W. Michell
Assistant Examiner—Lee S. Cohen
Attorney, Agent, or Firm—Hill, Gross, Simpson, Van Santen, Steadman, Chiara & Simpson

[57] ABSTRACT

A bipolar cutting electrode for high-frequency surgery having at least two mutually insulated and high-frequency voltage conductive metal portions which are at a fixed spacing relative to each other. The metal portions are metal tips which are located within the effective zone of the electrode in series in the cutting direction. When employing more than two metal tips, these should be positioned in a row extending along a semicircular arc which may also be formed, for example, in a lancette-shape.

2 Claims, 2 Drawing Figures

BIPOLAR CUTTING ELECTRODE FOR HIGH-FREQUENCY SURGERY

This is a continuation of application Ser. No. 570,792 filed Apr. 23, 1975, now abandoned.

FIELD OF THE INVENTION

The present invention relates to a bipolar cutting electrode for high-frequency surgery having at least two mutually insulated and high-frequency voltage conductive metal portions which are at a fixed spacing relative to each other.

DISCUSSION OF THE PRIOR ART

Currently known are curette-shaped cutting electrodes which are provided with a ball or spherically-shaped counterelectrode, and which are applied to the body of a patient externally of the effective zone of the active electrode. However, these electrodes, due to the relatively thick or heavy sphere of the counterelectrodes, as well as also the latters relatively large distance from the actual cutting electrode, are quite unwieldly and thereby also allow practically no smooth cutting paths. Their range of applicability is essentially restricted to the field of neuro-surgery.

SUMMARY OF THE INVENTION

Accordingly, it is an object of the present invention to obviate the disadvantages which are encountered in the prior art, and to provide a bipolar cutting electrode for highfrequency surgery which is essentially much more readily wielded, facilitates a smoother cutting path along the surface of the body as well as also in body incisions and which, viewed in general, finds much broader range of application than the currently known cutting electrodes.

The foregoing object is achieved in accordance with the present invention, in that the metal portions are metal tips which are located within the effective zone of the electrode in series in the cutting direction.

The serially or consecutively located cutting tips permit for a smoother cutting path, inasmuch as at least two successively located tips are always concurrently active during cutting. Since the metal tips which are futher within the effective zone of the electrode are immediately adjacent to each other, smaller effective surfaces are formed so that the electrode also during cutting, in general, becomes more wieldly, and is particularly well suited for the cutting on small surfaces, for example, also in body incisions.

In order to render possible the inclined support of the electrode during cutting, it is suitable that the metal tips be located so as to be offset relative to each other in the longitudinal direction of the electrode. When employing more than two metal tips, these should be positioned in a row extending along a semi-circular arc which may also be formed, for example, in a lancette-shape.

In a preferred embodiment of the inventive cutting electrode, the metal tips further should be formed of tapered ground ends of wires or pins, which are located within an insulating body so as to somewhat project therefrom in the cutting zone.

BRIEF DESCRIPTION OF THE DRAWING

Reference may now be had to the following detailed description of an exemplary embodiment of the invention, taken in conjunction with the accompanying drawing; in which.

DETAILED DESCRIPTION

Figure 1:
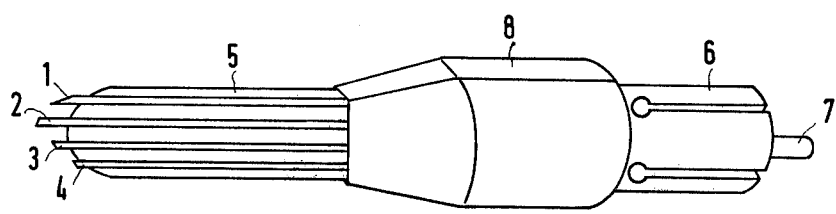
FIG. 1 illustrates, in a perspective view, a bipolar cutting electrode constructed pursuant to the present invention.

Referring now to the drawing, shown in FIG. 1 are cutting pins 1, 2, 3 and 4 which are constituted of metal such as, for example, molybdenum wire or the like, having a diameter of approximately 0.8 mm, and which are so located within an insulating body 5 which is formed, for example, of glass, as to somewhat project out of the insulating body at the forward end of the electrode (forward effective zone). The insulating body 5 is elongated and flat, as well as being rounded off at its front end. The pins 1 through 4, in correspondence with their tips following along the semi-circular arc, are more or less offset relative to each other in the longitudinal direction of the electrode.

Figure 2:
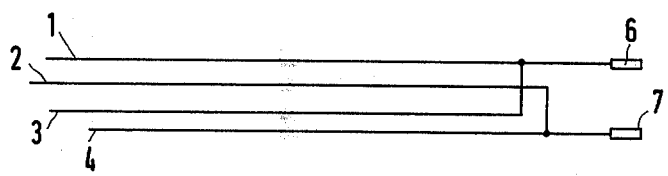
FIG. 2 is a schematic circuit showing the interconnection of the individual cutting tips of the electrode of FIG. 1.

The pins 1 through 4 are so interconnected, pursuant to FIG. 2, so that presently the pins 1 and 3 are connected pairwise to the terminal portion 6 for one pole, as well as the pins 2 and 4 being connected to the terminal 7 for connection to the other pole of a high-frequency source (not shown). In the inventive embodiment according to FIG. 1, the terminal or connector poles 6, 7 are constructed as a coaxial plug contact having an inner conductor 7 and an outer conductor 7. By means of the plug contact 6, 7, the electrode may preferably be selectively attached to a cable handpiece of a high-frequency surgical device. Electrode handpieces are known per se so as to obviate the need herein for a more detailed description thereof. As the transition piece between the actual cutting portion 1 through 5 of the electrode, as well as the electrode handpiece, the electrode according to FIG. 1 may be further encompassed by an additional insulating jacket 8 which is constituted of an insulating plastic material, for example, silicon rubber.

In the operative condition of the electrode of FIGS. 1 and 2 of the drawing, a high-frequency field always lies between two adjacent tips of the metal pins 1 through 4 which project out of the insulating body 5, and which may be utilized for separation of the tissues. The effective cutting surface between the individual pins is extremely small, so that the electrode is also suited for carrying out the smallest body cuts on the body surface as well as within body incisions or hollows. Since the cutting pins 1 through 4 are always located in series in a row along the cutting direction of the electrode, there is formed a correspondingly smooth cutting path.

The embodiment according to FIGS. 1 and 2 describes a preferred electrode having a total of four cutting pins. However, it is naturally conceivable that for other desired cutting shapes, through corresponding construction of the insulating body or, respectively, a corresponding arrangement of a greater or lesser number of metal pins, adjustments may be made to any desired type of application.

While there has been shown what is considered to be the preferred embodiment of the invention, it will be obvious that modifications may be made which come within the scope of the disclosure of the specification.

What is claimed is:

1. In a bipolar cutting electrode for high-frequency surgery, including a source of high frequency voltage, a plurality in excess of two, of mutually insulated, high-frequency voltage-conductive metallic tip potions in fixed spacing relative to each other, means for connecting said tip portions to said source of high frequency voltage, said metallic tip portions comprising ground ends of wire-shaped elements, an insulating member having a tip, said metallic tip portions being inserted into the tip of said insulating member so that the ground ends project therefrom forming the cutting zone of the electrode; the improvement comprising: said insulating member being substantially flat in the region of the cutting zone, said metallic tip portions being displaced relative to each other in the longitudinal direction of said electrode at the tip of said flat insulating member in a row along an arc, said cutting electrode being able to leave thereby a substantially smooth cut in a relatively narrow cavity of a body whereby a high frequency contact between at least two metallic tip portions is always maintained under an inclined holding of the cutting electrode.

2. Bipolar cutting electrode as claimed in claim 1, said metallic tip portions being formed of ground pin ends.

* * * * *